United States Patent [19]

Harris, III et al.

[11] Patent Number: 4,925,856

[45] Date of Patent: May 15, 1990

[54] ALDOXIME-SUBSTITUTED IMIDAZOLIUM DERIVATIVES USEFUL IN THE TREATMENT OF POISONING BY PHOSPHORUS-CONTAINING CHEMICALS

[75] Inventors: Ralph N. Harris, III, Redwood City, Calif.; Clifford D. Bedford, Silver Spring, Md.; Dane A. Goff, Menlo Park, Calif.; Duane E. Hilmas, Worthington, Ohio; Robert A. Howd, Rancho Cordova, Calif.; Richard A. Kenley, Libertyville, Ill.; Gary A. Koolpe, Mountain View, Calif.; Robert O. Pick, Walkersville, Md.

[73] Assignee: SRI International, Menlo Park, Calif.

[21] Appl. No.: 341,489

[22] Filed: Apr. 19, 1989

Related U.S. Application Data

[63] Continuation-in-part of Ser. No. 78,922, Jul. 28, 1987, abandoned.

[51] Int. Cl.$^5$ .................... A61K 31/44; C07D 401/06
[52] U.S. Cl. .................................... 514/341; 514/101; 514/397; 514/400; 546/278; 548/336; 548/343
[58] Field of Search ............... 548/343, 336; 546/278; 514/161, 397, 400, 341

[56] References Cited

PUBLICATIONS

Chemical Abstracts, 102:1630s(1985) [A. Miller, et al., Proc. West. Pharmacol. Soc. 1984, 27, 297–301].
Chemical Abstracts, 75:98534y (1971) [E. Glover, et al., J. Chem. Soc. c 1971, (16), 2748–9].
C. Bedford, et al., J. Med. Chem. 1984, 27, 1431.

Primary Examiner—Richard A. Schwartz
Attorney, Agent, or Firm—John P. Taylor

[57] ABSTRACT

A therapeutically effective class of low toxicity aldoxime-substituted functionalized imidazolium compounds and compositions is disclosed which is effective in the treatment of living species poisoned by organophosphorus chemicals which inactivate the enzyme acetylcholinesterase. In vivo administration of therapeutically effective amounts of these aldoxime-substituted imidazolium derivatives has been found to save mammals having inhibited acetylcholinesterase due to injection with lethal dosages of Soman.

19 Claims, No Drawings

ALDOXIME-SUBSTITUTED IMIDAZOLIUM DERIVATIVES USEFUL IN THE TREATMENT OF POISONING BY PHOSPHORUS-CONTAINING CHEMICALS

The invention described herein was made in the course of work under contracts DAMD17-82-C-2194 and DAMD17-85-C-5154 with the Department of Defense.

CROSS-REFERENCE TO RELATED APPLICATION

This application is a continuation in part of U.S. patent application Ser. No. 078,922, filed July 28, 1987 now abandoned.

BACKGROUND OF THE INVENTION

1. Field of the Invention

This invention relates to particular aldoxime salts useful in the treatment of poisoning by certain chemicals containing phosphorus. More particularly, this invention relates to particular classes of substituted imidazolium-2-aldoxime salts.

2. Description of the Related Art

Certain organic chemicals containing phosphorus including some agriculture chemicals (pesticides) such as parathion, chemical warfare agents such as Soman and Tabun, and other organo-phosphorus chemicals such as ethyl-p-nitrophenyl methylphosphonate (EPMP) attack the central nervous system of animals, including humans, and inactivate the body's naturally produced enzyme acetylcholinesterase, sometimes also called cholinesterase. This enzyme is used in living organisms to break down the naturally produced acetylcholine released by cholinergic neurons as a part of normal function of the autonomic nervous system.

Administration of the drug atropine has long been used as a treatment for the effects of such poisoning. For example, it increases the heart rate which would otherwise be decreased by an excess of acetylcholine in the system due to inactivation of the acetylcholinesterase enzyme which normally would immediately break down the acetylcholine. However, atropine cannot restore activity to (reactivate) the inhibited acetylcholinesterase. Other drugs, therefore, are conventionally administered with atropine to reactivate the acetylcholinesterase enzyme. Such drugs include toxogonin and 2-PAM, which contains the active agent 2-(hydroxyimino)methyl-1-methylpyridinium chloride.

Hagedorn U.S. Pat. Nos. 3,773,775 and 3,852,294 describe the use of (hydroxyimino)methylpyridinium compounds for treating and alleviating the symptoms of poisoning caused by exposure to phosphorus containing pesticides and war gases.

Poziomek et al., in an article entitled "Pyridinium aldoximes" published in the Journal of Organic Chemistry, Vol. 23 in 1958 at pp. 714–717, describe the preparation and testing of a number of pyridinium aldo ximes including 1,1'-polymethylenebis(4-formylpyridinium bromide) dioximes and N-substituted 2- and 4-formylpyridinium halide oximes and report that the bis-quaternary dioximes are active as chemotherapeutic agents in the treatment of acetylcholinesterase poisoning in experimental animals.

Wilson et al., in "A Specific Antidote Against Lethal Alkyl Phosphate Intoxification. V. Antidotal Properties", published in the Archives of Biochemistry and Biophysics, Vol. 69, in 1957 at pp. 468–474, discusses the effects of pyridine-2-aldoxime methiodide as an in vitro reactivator of alkyl phosphate-inhibited acetylcholinesterase.

However, these pyridine-based chemical agents are not always effective in reactivating the acetylcholinesterase enzyme, particularly when the body has been exposed to a large dosage of the acetylcholinesterase enzyme-inactivating chemical. Furthermore, the synthesis of at least some pyridine-based compounds requires the use of the known carcinogen bischloromethyl ether and a major requirement in the use of these oxime therapeutics is to guarantee to the Food and Drug Administration (FDA) in IND and NDA reports that no carcinogenic materials remain in the final product.

It was also found that attempts to produce some oxime-substituted pyridine-based chemicals resulted in the formation of derivatives which were relatively unstable and could not, therefore, be stored very long, which made their potential use as therapeutic agents dubious at best.

It is known that alkylimidazoles have therapeutic effects as treatment agents. Wilkinson et al., in "Structure-Activity Relationships in The Effects Of 1-alkylimidazoles On Microsomal Oxidation In Vitro And In Vivo", published in the Journal of Biochemical Pharmacology, Vol. 23 in 1974 at pp. 2377–2386, describes the biological activities of a number of 1-alkyl substituted imidazole compounds including activity as inhibitors of drug oxidation and potentiators of barbiturate sleeping time in mammals.

Iversen et al., in an article entitled "Preparation of 2-Imidazole and 2-Thiazolecarbaldehydes", published in ACTA Chem. Scand., Vol. 20, No. 10, in 1966, at pp. 2649–2657, report the preparation of a series of 2-imidazole- and 2-thioazolecarbaldehydes from imidazole and thiazole with the carbaldehyde in the 2-position.

The use of (hydroxyimino)methylimidazoles (aldoxime-substituted azolium derivatives) has also been explored by others for the treatment of organophosphorus poisoning in comparison to the pyridine-based 2-PAM standard treatment agent. Grifantini et al., in an article entitled "Structure-Activity Relationships in Reactivators of Organophosphorus-Inhibited Acetylcholinesterase V: Quaternary Salts of Hydroxyiminomethylimidazoles", published in the Journal of Pharmaceutical Sciences, vol. 64, No. 4, in 1972 at pp. 631–633, describes the effectiveness of quaternary salts of some derivatives of 2-(hydroxyimino)methylimidazole and 5-(hydroxyimino)methylimidazole on the reactivation of organophosphorus-inhibited acetylcholinesterase when inhibited by diethylphosphoryl and diisopropylphosphoryl groups. The reactivities of the two 2-(hydroxyimino)methylimidazole derivatives tested were respectively reported as a half and a fourth of that of 2-(hydroxyimino)methyl-1-methylpyridinium iodide (2-PAM).

Herrador et al., in an article entitled "Reactivators of Organophosphorus-Inhibited Acetylcholinesterase. 1. Imidazole Oxime Derivatives", published in the Journal of Medicinal Chemistry, Vol 28, in 1985 at pp. 146–149, discloses the synthesis and biological screening of 1-aryl(alkyl)-4-[(hydroxyimino)-methyl]-3-methylimidazolium iodides and 1-aryl(alkyl)-4-[(hydroxyimino)methyl]-3-methyl-2-(methylthio)-imidazolium iodides as potential reactivators of organophosphorus-inhibited acetylcholinesterase. All materials tested were reported as weak reactivators with the best ones said to be about two times less active than 2-PAM.

Bedford et al., in an article entitled "Structure-Activity Relationships for Reactivators of Organophosphorus-Inhibited Acetylcholinesterase: Quaternary Salts of 2-[(Hydroxyimino)methyl]imidazole" coauthored by some of us and published in the Journal of Medicinal Chemistry, Vol. 27, No. 11, 1984, at pages 1431-1438, discussed the in vitro testing of 1-methyl-2-(hydroxyimino)methyl-3-(alkoxy or aralkoxy)methyl-imidazolium chloride salts as reactivators of eel acetylcholinesterase inhibited by 3,3-dimethyl-2-butyl methylphosphonofluoridate (GD or Soman).

While the 2-[(hydroxyimino)methyl]imidazolium salts reported in this article have been subsequently found to be sufficiently effective in the treatment of acetylcholinesterase inhibited by organo-phosphorus compounds to save as high as 60% of mice injected with a lethal dose ($LD_{50}$) of Soman, it has also been found that the toxicity of such compounds is also quite high as determined by the low value of the $LD_{50}$ of the antidotal compound, i.e., the lower the amount of the antidotal compound which is lethal to 50% of the species to which it is administered, the more toxic the compound. When the antidotal compound has a low LD50, less of it can be safely administered to the species as an antidote to the organo-phosphoric chemical It, therefore, would be beneficial to provide a class of low toxicity, stable aldoxime-substituted imidazolium derivatives which would be more effective than standard pyridine-based treatment agents such as 2-PAM in the reactivation of the acetylcholinesterase enzyme and which would be capable of being produced without the use of precursors which are known carcinogens Surprisingly, despite the teachings of the prior art, we have discovered a class of stable aldoxime-substituted imidazolium derivatives which are more effective than 2-PAM in the reactivation of acetylcholinesterase and yet have low toxicity.

SUMMARY OF THE INVENTION

It is, therefore, an object of this invention to provide particular classes of low toxicity aldoxime-substituted imidazolium derivatives which are therapeutically effective in countering the inactivation of acetylcholinesterase by exposure of living species to toxic organophosphoric chemicals.

It is another object of the invention to provide a therapeutically effective treatment of living species to counter the inactivation of acetylcholinesterase by exposure to toxic organo-phosphoric chemicals.

It is yet another object of the invention to provide a therapeutically effective treatment of living species to counter the inactivation of acetylcholinesterase by exposure to toxic organophosphoric chemicals by the administration of a therapeutically effective amount of a low toxicity aldoxime-substituted imidazolium derivative.

These and other objects of the invention will be apparent from the following description

DETAILED DESCRIPTION OF THE INVENTION

In accordance with the invention, certain low toxicity aldoxime-substituted imidazolium derivatives are provided which are effective in the treatment of living species poisoned by organo-phosphoric chemicals which inactivate the enzyme acetylcholinesterase. These compounds have been found to be particularly effective in the treatment of living species having inhibited acetylcholinesterase due to poisoning by toxic organo-phosphorus compounds. For example, such compounds have been found to be clinically effective in saving mice from otherwise lethal dosages of Soman.

By the use of the terms "effective" and "effective amounts" when used herein to describe, for example, the in vivo treatment of living species, such as mammals, to counter the inactivation of the acetylcholinesterase, is meant an amount of an aldoxime-substituted imidazolium derivative which will be at least as effective as an equivalent dosage of 2-PAM, and preferably more effective than the equivalent amount of 2-PAM as measured in the number of mice surviving in vivo testing as will be discussed below.

By use of the term "low toxicity" is meant an aldoxime-substituted imidazolium derivative having an $LD_{50}$ of no less than about 0.1 millimoles/kg., and preferably no less than than about 0.25 millimoles/kg., i.e., at least about 0.1 millimoles, and preferably at least about 0.25 millimoles, of the compound must be administered per kilogram weight of the living species to result in 50% fatalities.

The aldoxime-substituted imidazolium derivatives of the invention comprise functionalized derivatives of quaternary and protic 2-(hydroxyimino)methyl-1,3-($R,R_1$)-trisubstituted imidazolium salts and 1,3,4-($R,R_1,R_2$)-tetrasubstituted imidazolium salts having the following formula:

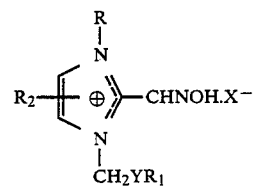

Formula I wherein:

Y is selected from the class consisting of methylene, oxygen, and sulfur;

R is selected from the class consisting of a 1-6 carbon alkyl, a 1-6 carbon alkenyl, and a 1-6 carbon alkynyl;

$R_1$, when Y equals methylene, is selected from the class consisting of nitro, azido, amido, halogen, loweralkylsulfonyl, sulfonamide, amino, dimethylamino, pyrrolidino, (3- or 4-carboxyamido)-1-pyridylmethyl, ethenyl, ethynyl, and a 1-6 carbon alkyl group substituted with loweralkylsulfonyl, halogen, nitro or azido;

$R_1$, when Y equals oxygen or sulfur, consists essentially of a 1-10 carbon alkyl group substituted with one or more substituents selected from the class consisting of nitro, azido, amido, halogen, loweralkylsulfonyl, sulfonamide, ethenyl, and ethynyl;

$R_2$ is a moiety in the 4 or 5 position selected from the class consisting of hydrogen, alkyl, alkenyl, alkynyl, alkoxyalkyl, and alkylthioalkyl, with each of said groups other than hydrogen having from 1-8 carbon atoms total and wherein any of the members of the class other than hydrogen may be substituted with one or more substituents selected from the class consisting of hydrogen, nitro, azido, amido, halogen, loweralkylsulfonyl, sulfonamide, amino, dimethylamino and pyrrolidino; and X is a therapeutically acceptable anion selected from the class consisting of a salt of an inorganic acid and a salt of an organic acid.

By the term "substituted with" is meant that the radical, where chemically possible, may have a further substitute group thereon selected from the list of substituents. It will be noted, in this regard, that the $R_2$ groups listed above may be optionally substituted with one or more of the groups listed, while the substituting or functionalizing of the $R_1$ groups are not stated to optional. This is because it has been found, in accordance with the invention, that substitution on the $R_1$ groups is necessary to achieve the desired low toxicity values which characterize the compounds of this invention from prior art aldoxime-substituted imidazolium compounds. Furthermore, it should be noted that for purposes of this definition, ethenyl and ethynyl are deemed to be substituted groups.

Examples of therapeutically acceptable salts of inorganic and organic acids used in forming the anion X include halide, sulfate, phosphate, tartrate, citrate, alkanesulfonate, arylsulfonate, perfluoroalkanesulfonate, succinate, acetate, malate, fumarate, or salicylate.

Particularly preferred imidazolium salts of the Formula I type include:

Compound 1: 1-[1'-(3'-butynyloxy)methyl]-2-(hydroxyimino)methyl-3-methylimidazolium chloride;

Compound 2: 2-(hydroxyimino)methyl-3-methyl-1-[1'-2'-(methylsulfonyl)ethyloxy)methyl]-imidazolium chloride;

Compound 3: 2-(hydroxyimino)methyl-3-methyl-1-[(2'-methyl-2'-nitropropyloxy)methyl]-imidazolium chloride;

Compound 4: 1-[(2'-N,N-dimethylaminium)-1'-ethyl]2-(hydroxyimino)methyl-3-methylimidazolium dichloride;

Compound 5: 1-[2'-(hydroxyimino)methyl-3'-methyl-1'-imidazolo]-3-(4''-carbamoyl-1''-pyridino)propane dichloride;

Compound 6: 1-(3'-bromopropyl-1'-oxy)methyl-2-(hydroxyimino)methyl-3-methylimidazolium chloride;

Compound 7: 2-(hydroxyimino)methyl-3-methyl-1-(2'-pyrrdidinium-1'-)ethylimidazolium chloride hydrochloride;

Compound 8: 1-(3'-butynyl-1'-thio)methyl-2-(hydroxyimino)methyl-3-methylimidazolium chloride;

Compound 9: 1-[(2'-N-ethyl-N-trifluoromethane sulfonyl)amino-1'-]ethyl-2-hydroxyimino)methyl-3-methylimidazolium chloride.

While we do not wish to be bound by any theory of how the compounds of the invention operate to counter the inactivation of acetylcholinesterase by organo-phosphorus chemicals, it is believed that the compounds of the invention may actually reactivate the acetylcholinesterase rather than merely treat the effects of such inactivation as does, for example, the drug atropine. In any event the use of the term "counter" herein is intended to mean that the compounds of the invention have an effect on the living species previously poisoned with an organo-phosphorus compound and then treated which is similar to the effect which would be expected if the acetylcholinesterase was reactivated.

The compounds of Formula I may be processed to all forms of preparations customary for pharmaceutical purposes. For example, pills, tablets, dragees, solutions, emulsions, syrups, and injection solutions can be produced therefrom. Suitable pharmaceutical excipients are those organic substances which are adapted for parenteral, enteral, or topical application and which do not react with the novel compounds, such as water, vegetable oils, polyethylene glycols, gelatin, lactose, amylose, magnesium stearate, talc, petroleum jelly such as Vaseline, cholesterol, etc. Especially suitable for parenteral application are solutions, preferably oily or aqueous solutions, as well as suspensions or emulsions. For enteral application, tablets or dragees may be employed For topical applications salves or creams which can be sterilized or mixed with auxiliary substances such as preservatives, stabilizers, or wetting agents, or salts for influencing the osmotic pressure, or with buffered substances are preferred.

The compound of the invention may be administered in dosages which range from 0.05 grams to 20 grams, depending upon the body weight of the mammals to which the compound will be administered, and can be administered as a single dose.

Each of the pharmaceutically active compounds of the invention may be incorporated, for oral administration, in a tablet as the sole active ingredient. A typical dosage tablet is constituted by from 1 to 3 wt. % binder, e.g., tragacanth; from 0.25 to 10 wt. % lubricant, e.g., talcum or magnesium stearate; an average dosage of active ingredient; and the balance consisting of a filler material, e.g., lactose. Tablets may be prepared using standard tableting techniques such as well known to those skilled in the art, employing the necessary amounts of conventional granulating liquids, e.g., alcohol SD-30 and purified water. An exemplary tableting formulation for the instant active compounds is as follows:

| Ingredient | Parts by Weight |
| --- | --- |
| Compounds of Formula I | 50 |
| Tragacanth | 2 |
| Lactose | 39.5 |
| Corn Starch | 5 |
| Talcum | 3 |
| Magnesium Stearate | 0.5 |
| Alcohol SD-30 q.s. | |
| Purified Water q.s. | |

Preparation of Formula I Compounds

Aldoxime-substituted imidazolium salts of the formula I type may be prepared by first preparing a 1-R-imidazole-2-carboxaldehyde following the lithiation procedure disclosed in the aforementioned Iversen et al. article (wherein R is selected from the class consisting of a 1-6 alkyl, a 1-6 alkenyl, a 1-6 alkynyl, and hydrogen as previously described above).

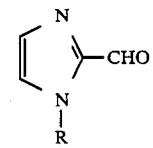

1-R-imidazole-2-carboxaldehyde

When $R_2$ is other than hydrogen, the 1-R-imidazole-2-carboxaldehyde precursor is then reacted with $R_5OH$ at 65° to 100° C. using an acid catalyst such as 4-toluene sulfonic acid to convert the precursor to the corresponding acetal derivative as shown in the formula below wherein $R_5$ represents either an open-chain acetal or a cyclic acetal.

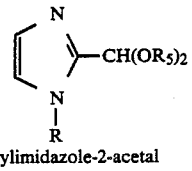

1-alkylimidazole-2-acetal

The acetal derivative is then lithiated at −40° to −20° C. by reacting it with an alkyl lithium reagent such as tert-butyllithium for 1 to 2 hours in an ethereal solvent such as tetrahydrofuran followed by reaction of the resulting 4(5)-lithiated intermediate at −78° to 25° C. with various electrophiles $R_2X$ for 2 to 4 hours wherein $R_2$ is selected from the class consisting of hydrogen, alkyl, alkenyl, alkynyl, alkoxyalkyl, and alkylthioalkyl, with each of said groups other than hydrogen having from 1–8 carbon atoms total and wherein any of the members of the class other than hydrogen may be substituted with one or more substituents selected from the class consisting of hydrogen, nitro, azido, amido, halogen, sulfonyl, sulfonamide, amino, dimethylamino and pyrrolidino as previously noted; and X is an anion such as a halide or other suitable leaving agent to form the trisubstituted imidazole precursor as shown below:

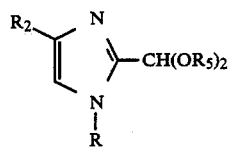

Trisubstituted Imidazole

Acid hydrolysis of the trisubstituted imidazole shown above by reacting it, for example, with an acid such as aqueous acetic acid for 2 to 4 hours at 80° to 100° C. will yield the corresponding aldehyde.

The 1-R-imidazole-2-carboxaldehyde precursor, which may also contain the 4(5) $R_2$ group as just described, is then reacted with hydroxylamine hydrochloride and alkali such as NaOH or $NaHCO_3$ in an alcoholic solvent at a temperature of 65° to 80° C. for a period of 2 hours to produce the following precursor:

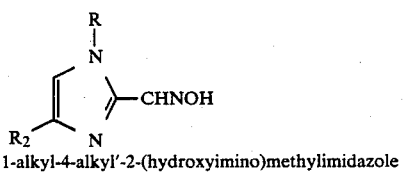

1-alkyl-4-alkyl'-2-(hydroxyimino)methylimidazole

The aldoxime-substituted imidazolium salts of the formula I type are then prepared by reacting the above formula I precursor with a compound $XCH_2YR_1$ in solution in a suitable liquid such as dry tetrahydrofuran which is added dropwise to the formula I precursor while maintaining the precursor at 0° to 25° C.

Compound $XCH_2YR_1$ is a reactant wherein, as previously noted above, Y is selected from the class consisting of methylene, oxygen, and sulfur; $R_1$, when Y equals methylene, is selected from the class consisting of nitro, azido, amido, halogen, sulfonyl, sulfonamide, amino, dimethylamino, pyrrolidino, (3- or 4-carboxyamido)-pyridyl, ethenyl, ethynyl, and a 1–6 carbon alkyl group substituted with sulfonyl, halogen, nitro or azido; $R_1$, when Y equals oxygen or sulfur, consists essentially of a 1–10 carbon alkyl group substituted with one or more substituents selected from the class consisting of nitro, azido, amido, halogen, sulfonyl, sulfonamide, ethenyl, and ethynyl; and X is a therapeutically acceptable anion selected from the class consisting of a salt of an inorganic acid and a salt of an organic acid.

The following examples, which describe the synthesis of a number of compounds of the invention and the in vivo testing of compounds of the invention, as well as 2-PAM, in mice injected with lethal doses of Soman, will serve to further illustrate the invention.

EXAMPLE 1

A. mixture consisting of 118.4 grams of 1-methylimidazole-2-carboxaldehyde, 82.5 grams of hydroxylamine hydrochloride, 113.9 grams of sodium bicarbonate and 1300 ml of absolute ethanol was heated under reflux for 2 hours and then filtered while still hot. The filtrate was concentrated to give a colorless residue which was recrystallized from 2-propanol to give 75 grams of 2-(hydroxyimino)methyl-1-methylimidazole as colorless crystals melting at 170°–172° C.

Into a stirring, ice-cooled mixture of 10.0 grams of 3-butyn-1-ol, 4.29 grams of s-trioxane and 50 ml of benzene was bubbled dry hydrogen chloride gas over a 2 hour period such that the temperature of the mixture did not exceed 10° C. After this time, there resulted a biphasic mixture from which the upper organic phase was separated and dried over calcium chloride. Vacuum distillation provided 8.27 grams of 1-chloromethoxy-3-butyne as a colorless liquid boiling at 80°–84° C. and 80 torr.

In 25 ml of dry dimethylformamide was dissolved 5.0 grams of the 2-(hydroxyimino)methyl-1-methylimidazole made above and the resulting mixture was treated dropwise while being stirred with a solution of 8.2 grams of the 1-chloromethoxy-3butyne made above in 125 ml of dry tetrahydrofuran. After being stirred for 48 hours, the mixture was filtered to give a white solid which was washed well with diethyl ether. Upon recrystallization of the solid from ethanol/ethyl acetate, there was obtained 8.06 grams of 1-[1'-(3'-butynyloxy)methyl]-2-(hydroxyimino)methyl-3-methylimidazolium chloride as a colorless, crystalline solid melting at 128°–129° C.

EXAMPLE 2

Into a continuously stirred suspension of 15.0 g of 2-(methylsulfonyl)ethanol, 3.63 g of s-trioxane, and 75 ml of benzene was bubbled dry hydrogen chloride gas at room temperature over a period of 3.5 hours. After this time, a biphasic mixture resulted from which the upper organic phase was separated, dried over sodium sulfate, and bubbled with nitrogen to remove excess hydrogen chloride. After concentrating, the remaining oil was vacuum distilled to provide 10.6 g of 1-chloromethoxy-2-(methylsulfonyl)ethane as a colorless oil boiling at 132°–135° C. and 0.1 torr.

To a continuously stirred mixture of 5.5 g of 2-(hydroxyimino)methyl-1-methylimidazole in 30 ml of dry dimethylformamide was added a mixture of 10.6 g of 1-chloromethoxy-2-(methylsulfonyl)ethane prepared above in 150 ml of dry tetrahydrofuran (THF). After being stirred for 12 hours at room temperature, the mixture was filtered to give a solid which was washed well with diethyl ether and recrystallized from methanol/ethyl acetate to give 2-(hydroxyimino)methyl-3- methyl-1-[1'-(2'-methylsulfonyl)ethyloxy]methylimidazolium chloride as a white solid melting at 161°-162° C. with decomposition.

EXAMPLE 3

Into a continuously stirred mixture of 20.0 g of 2-methyl-2-nitro-1-propanol, 5.05 g of S-trioxane, and 100 ml of benzene was bubbled dry hydrogen chloride gas over a 2.5 hour period. After this time, there resulted a biphasic mixture from which the upper organic phase was separated, dried over sodium sulfate, and bubbled with nitrogen to remove excess hydrogen chloride. After concentrating the organic layer, the remaining oil was vacuum distilled to provide 19.9 grams of 1-chloromethoxy-2-methyl-2-nitropropane as a colorless oil boiling at 48°-49° C. and 0.25 torr.

To a continuously stirred solution of 5.5 g of 2-(hydroxyimino)methyl-1-methylimidazole in 30 ml of dry dimethylformamide was added a solution of 1-chloromethoxy-2-methyl-2-nitropropane prepared above in 150 ml of dry THF. After being stirred at room temperature for 3 days, the mixture was filtered to give a solid which was washed with diethyl ether and recrystallized from ethanol/ethyl acetate to provide 7.0 g of 2-(hydroxyimino)methyl-3-methyl-1-[(2'-methyl-2'-nitropropyloxy)methyl]-imidazolium chloride as white crystals melting at 172°-173° C. with decomposition.

The preceding examples can be repeated with similar success by substituting the generically or specifically prescribed reactants and/or operating conditions of this invention described elsewhere in this specification for those used in the preceding examples.

The following example will serve to illustrate the biological activities of the aldoxime-substituted imidazolium derivatives of the invention made in Examples 1-3 when tested under in vivo conditions.

EXAMPLE 4

To show the in vivo biological effectiveness of the aldoxime-substituted imidazolium derivatives of the invention in countering the effects of the inactivated acetylcholinesterase enzyme, a number of mice were treated with twice the lethal dosage ($LD_{50}$) of Soman, where $LD_{50}$ is defined as the dosage at which 50% of the mice injected will die, and then injected intramuscularly with 11.5 milligrams per kilogram of body weight of atropine sulfate. Some of these mice were then respectively injected intramuscularly with varying amounts of three compounds of the invention previously identified herein as preferred compounds 1-3, and respectively, prepared in examples 1-3. Others of the mice injected above with Soman were injected with similar amounts of 2-PAM as a control. Other mice injected with Soman, as described above, were injected with 1(2',2'-dimethylpropyloxy)methyl-2-(hydroxyimino)-methyl-3-(1''-propyl)imidazolium chloride, a side-chain unfunctionalized aldoxime-substituted imidazolium compound similar to the compounds described in the Bedford et al. article and identified in Table I as "prior art imidazolium".

The amount of the respective dosages were 1/16, ⅛, and ¼ of the lethal dosage which is shown in Table I as $LD_{50}$, i.e., the dosage amount of the treatment compound at which 50% of the mice injected will die. This amount will vary for each compound and therefore is separately listed in the table below in millimoles of compound/body weight of the mouse in kilograms.

The numbers listed in the survival columns are the percentage of ten mice which survived after being treated with the indicated fraction of the lethal dosage of the reactivating treatment agent, i.e., 2-PAM, the prior art imidazolium, or one of the aldoxime-substituted imidazolium derivatives of the invention. It will be noted that none of the mice treated with 2-PAM, in the amounts listed, survived.

TABLE I

| Sample Compound Number | $LD_{50}$ (millimoles per kg) | Survival Dosage 1/16 | ⅛ | ¼ |
|---|---|---|---|---|
| 2-PAM | 0.64 | 0 | 0 | 0 |
| Prior Art Imidazolium | 0.09 | 20 | 80 | 70 |
| 1 | 0.62 | 30 | 80 | 90 |
| 2 | 2.7 | 90 | 70 | 60 |
| 3 | 0.31 | 80 | 90 | 60 |

Thus, the results indicate that all of the samples of the compounds of the invention tested in vivo in mice showed superior results over the 2-PAM control, indicating that the compounds of the invention possess superior capabilities for countering the inactivation of acetylcholinesterase by poisoning with organophosphorus chemical agents.

Furthermore, in comparing samples 1-3 of the invention with the prior art imidazolium compound, it will be seen that while the prior art imidazolium compound could be administered in an amount while would save 80% of the mice previously injected with Soman, the $LD_{50}$ dosage level for the prior art imidazolium compound was very low (almost ¼ of the $LD_{50}$ of compound 3 of the invention which is the lowest of compounds 1-3), indicating the much higher level of toxicity of the prior art unfunctionalized imidazolium compounds.

Similar results have also been obtained in in vivo tests conducted in mice infected with lethal doses of Tabun.

EXAMPLE 5

To a continuously stirred mixture of 3.01 ml of N,N-dimethylethanolamine in 125 ml of dichloromethane cooled at −78° C. was added dropwise 5.08 ml of trifluoromethanesulfonic (triflic) anhydride over a 10 minute period. The mixture was allowed to warm to 0° C. and stirred for 30 minutes whereupon the solvent was evaporated in vacuo. The remaining residue was diluted with 125 ml of nitromethane and there was added 3.44 grams of 2-(hydroxyimino)-methyl-1-methylimidazole. The cooling bath was then removed and the mixture allowed to stir for 15 hours at room temperature. After the mixture was concentrated in vacuo, the remaining residue was Cl-anion exchanged to give a solid that was recrystallized twice from ethanol-ethyl acetate to give 3.01 grams of pure 1-[(2'-N,N-dimethylaminium)-1'-ethyl]-2-(hydroxyimino)methyl-3-methylimidazolium dichloride as a colorless, crystalline solid melting at 230°-231° C.

EXAMPLE 6

A mixture of 7.61 grams of 1,3-propanediol and 13.94 ml of triethylamine in 30 ml of dichloromethane was added dropwise to a continuously stirred mixture of 7.74 ml of methanesulfonyl chloride in 80 ml of dichloromethane cooled at 0° C. After being stirred in the cold for 2 hours, the mixture was concentrated in vacuo and the residue passed through 100 grams of silica gel and eluted first with dichloromethane-ethyl acetate (4:1) to elute 1,3-propyl bis-methanesulfonate and then with dichloromethane-ethyl acetate (1:4) to elute 6.07 grams of pure 3-hydroxy-1-propyl methanesulfonate as a colorless oil.

To a solution of 6.05 grams of 3-hydroxy-1-propyl methanesulfonate prepared above, in 25 ml of dichloromethane cooled at −20° C., was added 3.17 ml of pyridine. The mixture was then added via cannula over a 40 minute period to a stirred solution of 6.64 ml of triflic anhydride in 50 ml of dichloromethane cooled at 0° C. After being stirred for 15 minutes, the mixture was washed with two 50 ml portions of water, dried over magnesium sulfate, filtered and concentrated in vacuo to give a tan oil. The oil was flash-chromatographed on silica gel and eluted with dichloromethane to provide 8.91 grams of pure 3-methanesulfonyloxy-1-(trifluoromethanesulfonyloxy)propane as a colorless oil.

To a continuously stirred suspension of 3.75 grams of 2-(hydroxyimino)-methyl-1-methylimidazole in 120 ml of nitromethane cooled at 0° C. was added a solution of 8.66 grams of 3-methanesulfonyloxy-1-(trifluoromethanesulfonyloxy)-propane prepared above in 10 ml of nitromethane. The cooling bath was removed and, after the mixture was stirred at room temperature for 1 hour, there was then added 3.66 grams of isonicotinamide. The mixture was stirred for two months at 35° C. and then at 80° C. for four days. The solvent was removed in vacuo and the remaining residue Cl-anion exchanged in deionized water. After washing the aqueous solution with ethyl acetate, the water was removed under reduced pressure to provide a brown foam that was recrystallized twice from ethanol-ethyl acetate. There was obtained 5.43 grams of pure 1-[2'-(hydroxyimino)-methyl-3'-methyl-1'-imidazolo]-3-(4''-carbamoyl-1''-pyridino)propane dichloride as a colorless, crystalline solid melting at 220°–221° C. with decomposition.

EXAMPLE 7

To show the in vivo biological effectiveness of the aldoxime-substituted imidazolium derivatives of the invention formed in Examples 5 and 6 above in countering the effects of the inactivated acetylcholinesterase enzyme, a number of mice were treated with twice the lethal dosage (LD$_{50}$) of Soman, and then injected intramuscularly with 11.5 milligrams per kilogram of body weight of atropine sulfate, as in Example 4. Some of these mice were then respectively injected intramuscularly with varying amounts of preferred compounds 4 and 5 respectively prepared in examples 4 and 5. Others of the mice injected above with Soman were injected with similar amounts of 2-PAM as a control.

The amount of the respective dosages were 1/256, 1/32, and ¼ of the lethal dosage which is shown in Table II as LD$_{50}$, i.e., the dosage amount of the treatment compound at which 50% of the mice injected will die. This amount will vary for each compound and therefore is separately listed in the table below in millimoles of compound/body weight of the mouse in kilograms as in Table I.

The numbers listed in the survival columns in Table II are the percentage of ten mice which survived after being treated with the indicated fraction of the lethal dosage of the reactivating treatment agent. It will be noted again that none of the mice treated with 2-PAM, in the amounts listed, survived.

TABLE II

| Sample Compound Number | LD$_{50}$ (millimoles per kg) | Survival Dosage | | |
|---|---|---|---|---|
| | | 1/256 | 1/32 | ¼ |
| 2-PAM | 0.64 | 0 | 0 | 0 |
| 4 | 1.49 | 0 | 0 | 100 |
| 5 | 1.06 | 10 | 70 | 100 |

EXAMPLE 8

To show the in vivo biological effectiveness of the aldoxime-substituted imidazolium derivatives of the invention of preferred compounds 6–10, previously identified above, in countering the effects of the inactivated acetylcholinesterase enzyme, a number of mice were treated with twice the lethal dosage (LD$_{50}$) of either Soman or Tabiun, and then injected intramuscularly with 11,5 milligrams per kilogram of body weight of atropine sulfate, as in Example 4. The mice were then respectively injected intramuscularly with varying amounts of preferred compounds 6–10.

The amount of the respective dosages were 1/16, 1/10, and ¼ of the lethal dosage which is shown in Table III as LD$_{50}$, i.e., the dosage amount of the treatment compound at which 50% of the mice injected will die. This amount will vary for each compound and therefore is separately listed in the table below in millimoles of compound/body weight of the mouse in kilograms as in Tables 1 and II.

As in Tables I and II above, the numbers listed in the survival columns in Table III are the percentage of ten mice which survived after being treated with the indicated fraction of the lethal dosage of the reactivating treatment agent.

TABLE III

| Sample Compound Number | LD$_{50}$ (millimoles per kg) | Survival | | | |
|---|---|---|---|---|---|
| | | Soman Dosage | | Tabiun Dosage | |
| | | 1/16 | ¼ | 1/10 | ¼ |
| 6 | 0.680 | 20 | 40 | — | — |
| 7 | 0.580 | 10 | 70 | 0 | 10 |
| 8 | 0.430 | 10 | 60 | 0 | 60 |
| 9 | 0.283 | 100 | 50 | 80 | 70 |

Thus, the invention provides pharmaceutically acceptable, functionalized aldoxime-substituted imidazolium derivatives which are more effective than standard pyridine-based chemicals in in vivo reactivation of acetylcholinesterase inactivated by exposure to toxic organophosphorus chemicals and which have lower toxicity than unfunctionalized aldoxime-substituted imidazolium compounds. From the foregoing description, one skilled in the art can easily ascertain the essential features of this invention, and without departing from the spirit and scope thereof, can make various changes and modification of the invention to adapt it to various usages and conditions. All such changes and modification should therefore be deemed to be within the scope of the invention which is limited only by the scope of the following claims.

What is claimed is:

1. A compound having the following formula:

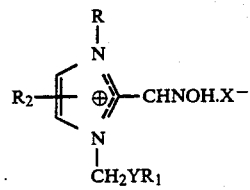

wherein:
Y is selected from the class consisting of methylene, oxygen, and sulfur;
R is selected from the class consisting of a 1-6 carbon alkyl, a 1-6 carbon alkenyl, and a 1-6 carbon alkynyl;
$R_1$, when Y equals methylene, is selected from the class consisting of nitro, azido, amido, halogen, loweralkylsulfonyll, sulfonamide, amino, dimethylamino, pyrrolidino, (3- or 4-carboxyamido)-1-pyridylmethyl, ethenyl, ethynyl, and a 1-6 carbon alkyl group substituted with loweralkylsulfonyll, halogen, nitro or azido;
$R_1$, when Y equals oxygen or sulfur, is a 1-10 carbon alkyl group substituted with one or more substituents selected from the class consisting of nitro, azido, amido, halogen, loweralkylsulfonyl, sulfonamide, ethenyl, and ethynyl;
$R_2$ is a moiety in the 4 or 5 position selected from the class consisting of hydrogen, alkyl, alkenyl, alkynyl, alkoxyalkyl, and alkylthioalkyl, with each of said groups other than hydrogen having from 1-8 carbon atoms total and wherein any of the members of the class other than hydrogen may be substituted with one or more substituents selected from the class consisting of hydrogen, nitro, azido, amido, halogen, loweralkylsulfonyl, sulfonamide, amino, dimethylamino and pyrrolidino; and
X is a therapeutically acceptable anion selected from the class consisting of a salt of an inorganic acid and a salt of an organic acid.

2. The compound of claim 1 wherein the anion represented by X is selected from the class consisting of halide, sulfate, phosphate, tartrate, citrate, alkanesulfonate, arylsulfonate, perfluoroalkanesulfonate, succinate, acetate, malate, fumarate, and salicylate anions.

3. The compound of claim 1 wherein Y is oxygen.

4. The compound of claim 1 which is 1-[1'(3'-butynyloxy)methyl]-2-(hydroxyimino)methyl-3-methylimidazolium chloride.

5. The compound of claim 1 which is 2-(hydroxyimino)methyl-3-methyl-1l-[1'-(2'-methylsulfonylethyloxy)methyl]imidazolium chloride.

6. The compound of claim 1 which is 2-(hydroxyimino)methyl-3-methyl-1-[(2'-methyl-2'-nitropropyloxy)methyl]imidazolium chloride.

7. The compound of claim 1 which is 1-[(2'-N,N-dimethylaminium)-1'-ethyl]-2-(hydroxyimino)methyl-3-methylimidazolium dichloride.

8. The compound of claim 1 which is 1-[2'-(hydroxyimino)methyl-3'-methyl-1'-imidazolo]-3-(4''-carbamoyl-1''-pyridino)propane dichloride.

9. The compound of claim 1 which is 1-(3'-bromopropyl-1'-oxy)methyl-2-(hydroxyimino)methyl-3-methylimidazolium chloride.

10. The compound of claim 1 which is 2-(hydroxyimino)methyl-3-methyl-1-(2'-pyrrolidinium-1'-)ethylimidazolium chloride hydrochloride.

11. The compound of claim 1 which is 1-(3'-butynyl-1'-thio)methyl-2-(hydroxyimino)methyl-3-methylimidazolium chloride.

12. The compound 1-[(2'-N-ethyl-N-trifluoromethane sulfonyl)amino-1'-]ethyl-2(hydroxyimino)methyl-3-methylimidazolium chloride.

13. A therapeutically effective low toxicity composition capable of countering the inactivation of acetylcholinesterase in living species poisoned by organophosphorus chemicals said composition comprising:
(a) a therapeutically effective amount of a compound having the following formula:

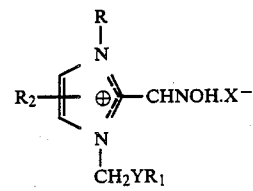

wherein:
Y is selected from the class consisting of methylene, oxygen, and sulfur;
R is selected from the class consisting of a 1-6 carbon alkyl, a 1-6 carbon alkenyl, and a 1-6 carbon alkynyl;
$R_1$, when Y equals methylene, is selected from the class consisting of nitro, azido, amido, halogen, loweralkylsulfonyl, sulfonamide, amino, dimethylamino, pyrrolidino, (3- or 4-carboxy-amido)-1-pyridylmethyl, ethenyl, ethynyl, and a 1-6 carbon alkyl group substituted with loweralkylsulfonyll, halogen, nitro or azido;
$R_1$, when Y equals oxygen or sulfur, is a 1-10 carbon alkyl group substituted with one or more substituents selected from the class consisting of nitro, azido, amido, halogen, loweralkylsulfonyll, sulfonamide, ethenyl, and ethynyl;
$R_2$ is a moiety in the 4 or 5 position selected from the class consisting of hydrogen, alkyl, alkenyl, alkynyl, alkoxyalkyl, and alkylthioalkyl, with each of said groups other than hydrogen having from 1-8 carbon atoms total and wherein any of the members of the class other than hydrogen may be substituted with one or more substituents selected from the class consisting of hydrogen, nitro, azido, amido, halogen, loweralkylsulfonyl, sulfonamide, amino, dimethylamino and pyrrolidino; and
X is a therapeutically acceptable anion selected from the class consisting of a salt of an inorganic acid and a salt of an organic acid; and
(b) a pharmaceutical excipient which includes one or more members selected from the class consisting of water, vegetable oils, polyethylene glycols, gelatin, lactose, amylose, magnesium stearate, talc, petroleum jelly, and cholesterol.

14. The therapeutically effective composition of claim 13 wherein the $LD_{50}$ dosage of the compound is greater than 0.1 millimoles/kg.

15. The therapeutically effective composition of claim 13 wherein the $LD_{50}$ dosage of the compound is greater than 0.25 millimoles/kg.

16. A method of reactivating acetylcholinesterase enzyme in living tissue inactivated by exposure to an organophosphorus chemical which comprises treating a mammal in vivo with a therapeutically effective amount of a low toxicity composition capable of countering inactivated acetylcholinesterase in living species po